(12) United States Patent
Lin

(10) Patent No.: US 10,869,988 B2
(45) Date of Patent: Dec. 22, 2020

(54) GAS GENERATOR

(71) Applicant: Hsin-Yung Lin, Taoyuan (TW)

(72) Inventor: Hsin-Yung Lin, Taoyuan (TW)

( * ) Notice: Subject to any disclaimer, the term of this patent is extended or adjusted under 35 U.S.C. 154(b) by 360 days.

(21) Appl. No.: 15/751,017

(22) PCT Filed: Aug. 3, 2016

(86) PCT No.: PCT/CN2016/092990
§ 371 (c)(1),
(2) Date: Feb. 7, 2018

(87) PCT Pub. No.: WO2017/024969
PCT Pub. Date: Feb. 16, 2017

(65) Prior Publication Data
US 2018/0228995 A1  Aug. 16, 2018

(30) Foreign Application Priority Data

Aug. 11, 2015  (CN) .......................... 2015 1 0488043

(51) Int. Cl.
*A61M 16/12* (2006.01)
*C25B 15/08* (2006.01)
(Continued)

(52) U.S. Cl.
CPC ........ *A61M 16/122* (2014.02); *A61M 16/021* (2017.08); *A61M 16/10* (2013.01);
(Continued)

(58) Field of Classification Search
CPC .............. A61M 16/122; A61M 16/105; A61M 16/1005; C25B 1/04
See application file for complete search history.

(56) References Cited

U.S. PATENT DOCUMENTS 5,209,906 A * 5/1993 Watkins ................. B01J 8/0285
165/163
5,865,171 A * 2/1999 Cinquin ............... A61M 11/005
128/200.14
(Continued)

FOREIGN PATENT DOCUMENTS

CN  201912599  8/2011
CN  103785091  5/2014
(Continued)

OTHER PUBLICATIONS

Search Report and Written Opinion dated Oct. 17, 2016 for PCT Application No. PCT/CN2016/092990.
(Continued)

*Primary Examiner* — LaToya M Louis

(57) ABSTRACT

A gas generator includes a water tank, an electrolysis device, a condensate filter, a humidification device, and a pump device. The electrolysis device is coupled to the water tank to electrolyze electrolyzed water accommodated in the water tank to generate a hydrogen-oxygen mixed gas. The hydrogen-oxygen mixed gas is condensed and filtered out electrolyte in the hydrogen-oxygen mixed gas by the condensate filter to generate a filtered hydrogen-oxygen mixed gas. The humidification device accommodates supplementary water and is connected to the condensate device for humidifying the filtered hydrogen-oxygen mixed gas, The supplementary water is pumped back to the water tank from the humidification device by the pump device; therefore, the electrolyte absorbed in the condensate filter is flushed back to the water tank for reducing the consumption of the electrolyte.

13 Claims, 18 Drawing Sheets

(51) Int. Cl.

| | | |
|---|---|---|
| *C25B 1/04* | (2006.01) | |
| *A61M 16/00* | (2006.01) | |
| *A61M 16/10* | (2006.01) | |
| *A61M 16/16* | (2006.01) | |
| *B01D 53/04* | (2006.01) | |
| *B01D 53/26* | (2006.01) | |
| *A61M 16/20* | (2006.01) | |
| *A61M 16/08* | (2006.01) | |

(52) U.S. Cl.
CPC ...... *A61M 16/105* (2013.01); *A61M 16/1005* (2014.02); *A61M 16/12* (2013.01); *A61M 16/16* (2013.01); *B01D 53/0407* (2013.01); *B01D 53/265* (2013.01); *C25B 1/04* (2013.01); *C25B 15/08* (2013.01); *A61M 16/0816* (2013.01); *A61M 16/0875* (2013.01); *A61M 16/0883* (2014.02); *A61M 16/208* (2013.01); *A61M 16/209* (2014.02); *A61M 2202/0208* (2013.01); *A61M 2205/07* (2013.01); *A61M 2205/3334* (2013.01); *A61M 2205/3379* (2013.01); *A61M 2205/3606* (2013.01); *A61M 2205/7536* (2013.01); *A61M 2205/8231* (2013.01); *A61M 2209/084* (2013.01); *B01D 2253/102* (2013.01); *Y02E 60/36* (2013.01)

(56) References Cited

U.S. PATENT DOCUMENTS

| | | | | |
|---|---|---|---|---|
| 9,101,941 | B2* | 8/2015 | Kim | C01B 32/354 |
| 9,937,275 | B2* | 4/2018 | Cadieux | A61L 2/202 |
| 2002/0076371 | A1* | 6/2002 | Foster | B01J 19/088 |
| | | | | 422/186.04 |
| 2006/0046113 | A1* | 3/2006 | Wang | B01J 19/249 |
| | | | | 48/61 |
| 2008/0314741 | A1 | 12/2008 | Balestrino et al. | |
| 2010/0064892 | A1 | 3/2010 | Linsday | |
| 2010/0236921 | A1* | 9/2010 | Yang | C25B 1/04 |
| | | | | 204/264 |
| 2013/0133656 | A1* | 5/2013 | Nightingale | A61M 16/109 |
| | | | | 128/204.23 |
| 2013/0206586 | A1* | 8/2013 | Lin | C25B 15/02 |
| | | | | 204/228.2 |
| 2014/0360496 | A1* | 12/2014 | Reese | A61M 16/1005 |
| | | | | 128/200.28 |
| 2015/0190604 | A1 | 7/2015 | Lin | |
| 2015/0211131 | A1 | 7/2015 | Jacobs | |
| 2016/0090657 | A1* | 3/2016 | Nigel | C25B 1/08 |
| | | | | 205/638 |
| 2016/0281241 | A1* | 9/2016 | Higashi | H01L 31/0749 |

FOREIGN PATENT DOCUMENTS

| | | |
|---|---|---|
| CN | 205055130 | 3/2016 |
| CN | 105498065 | 4/2016 |
| CN | 105617503 | 6/2016 |
| CN | 105624723 | 6/2016 |
| CN | 105624724 | 6/2016 |
| EP | 2039805 | 3/2009 |
| EP | 3095764 | 11/2016 |
| JP | 3192728 U | 8/2014 |
| JP | 3193761 | 10/2014 |
| JP | 2014223590 | 12/2014 |
| KR | 20000061955 | 10/2000 |
| KR | 20060100528 A | 9/2006 |
| KR | 20140147723 A | 12/2014 |
| TW | 450942 | 8/2001 |
| TW | I332037 | 10/2010 |
| TW | 201500069 | 1/2015 |
| TW | 201522714 | 6/2015 |
| TW | M503226 | 6/2015 |
| WO | WO2014170337 | 10/2014 |
| WO | WO20140170337 | 10/2014 |
| WO | WO2017024969 | 2/2017 |

OTHER PUBLICATIONS

Search Report dated Mar. 19, 2019 for European Application No. 16834593.2.
Search Report and Written Opinion dated Jul. 30, 2018 for Singapore Application No. 11201801139T.

* cited by examiner

GAS GENERATOR

BACKGROUND OF THE INVENTION

CROSS-REFERENCE TO RELATED APPLICATIONS

This application is a U.S. National Phase of International Application No. PCT/CN2016/092990, filed Aug. 3, 2016 which claims the priority benefit of Chinese Application Serial No. 201510488043.3 filed Aug. 11, 2015 the disclosure of which is incorporated herein by reference.

1. Field of the Invention

The present invention relates to a gas generator, and more particularly, to a gas generator which can provide the function of filtering and humidification, and reduces the consumption of the electrolyte.

2. Description of the Prior Art

As people have always been paying much attention on health developments, many developments in medical technology are often targeted on treating diseases and prolonging human life. Also, most of the treatments in the past are passive, which means that the disease is treated only when it occurs, and the treatments may include an operation, a medication treatment, a radiation therapy, or a medical treatment for cancer. However, in recent years, most of the medical experts' researches are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and are becoming increasingly popular to the general public.

Studies have found that there are instable oxygen species ($O^+$), also known as free radicals, in the human body. The free radicals are usually generated due to diseases, diet, and environment. And, one's lifestyle can be excreted in the form of water by reacting with the inhaled hydrogen. With this method, the amount of free radicals in the human body can be reduced, thereby restoring the body condition from an acidic state to an alkaline state, to achieve an anti-oxidation, anti-aging and beauty health effect, and even to eliminate chronic diseases. Furthermore, there are also clinical experiments showing that patients who need to inhale a high concentration of oxygen for an extended period of time would experience lung damage. However, it could be ameliorated by inhaling hydrogen.

General electrolysis device generates high temperature in the electrolyzing process, which will decrease the efficiency of electrolyzing and cause energy consumption problems; furthermore, the hydrogen-oxygen mixed gas becomes unsuitable for the user to inhale. Although the problems mentioned above can be solved through replenishing supplementary water or the electrolyte continuously, it also makes the operation of the electrolysis device inconvenient.

SUMMARY OF THE INVENTION

Therefore, the present inventor with many years engaged in the manufacture and development of related products and design experience went through the detailed design and careful assessment to finally confirm that the present invention is practically usable.

The present invention provides a gas generator for electrolyzing water and generating the hydrogen-oxygen mixed gas, meanwhile the electrolyte in the hydrogen-oxygen mixed gas is condensed and filtered. The gas is humidified to reduce the amount of the electrolyte in the hydrogen-oxygen mixed gas to make it be able to be inhaled by the user. Moreover, by replenishing the supplementary water and flushing the electrolyte back into the electrolysis device to restore the filtering function of the circulating passageway. It can not only avoid the block and corrosion in the circulating passageway but also reduce the consumption of the electrolyte.

The present invention provides a gas generator comprising the water tank, the electrolysis device, the condensate filter, the humidification device and the pump device. The water tank accommodates electrolyzed water, wherein the electrolyzed water comprises electrolyte. The electrolysis device is coupled to the water tank for electrolyzing the electrolyzed water to generate a hydrogen-oxygen mixed gas. The condensate filter is connected to the electrolysis device for condensing the hydrogen-oxygen mixed gas generated at the electrolysis device and filtering the electrolyte in the hydrogen-oxygen mixed gas for generating the filtered hydrogen-oxygen mixed gas. The humidification device connected to the condensate filter accommodates the supplementary water for humidifying the filtered hydrogen-oxygen mixed gas. The pump device is connected to the water tank for generating negative pressure in the water tank in order to pump back the supplementary water from the humidification device through the condensate filter into the water tank, and the electrolyte adsorbed in the condensate filter is back flushed to the water tank. When the flow rate of generating the hydrogen-oxygen mixed gas by the gas generator is 600 L/hr after operating 40 to 60 hours, the loss of the electrolyte is equal to or less than 5 g.

Furthermore, the present invention provides a gas generator which selectively comprises an atomized gas mixing tank. The atomized gas mixing tank comprises a gas outlet. The water tank and the atomized gas mixing tank are connected to the by the pump device. When the pump device is in operation, the gas in the water tank is pumped out through the gas outlet of the atomized gas mixing tank to generate a negative pressure in the water tank.

The atomized gas mixing tank is selectively connected to the humidification device for receiving a humidified hydrogen-oxygen mixed gas. The atomized gas mixing tank generates an atomized gas mixed with the humidified hydrogen-oxygen mixed gas to generate a healthy gas for a user to inhale. The atomized gas comprises at least one of water vapor, atomized liquid, volatile purified oils or combinations thereof.

The humidification device selectively comprises at least an output tube. The output tube comprises a plurality of holes. The hydrogen-oxygen mixed gas is pumped out from the plurality of holes of the output tube to humidify the filtered hydrogen-oxygen mixed gas.

The condensate filter selectively comprises a plurality of the condensate plates. Every condensate plate comprises a passageway. The passageway of the condensate plate is connected to the passageway of the adjacent condensate plate to form a circulating passageway for circulating the hydrogen-oxygen mixed gas.

Furthermore, the present invention further provides a gas generator which comprises a water tank, an electrolysis device, a condensate filter, a humidification filter, a humidification device and a pump device. The water tank accommodates electrolyzed water. The electrolyzed water comprises an electrolyte. The electrolysis device is coupled to the water tank for electrolyzing electrolyzed water to generate a hydrogen-oxygen mixed gas. The humidification filter connected to the condensate filter accommodates water and filter the filtered hydrogen-oxygen mixed gas which is filtered by the condensate filter. The humidification device is connected to the humidification filter accommodates a supplementary water for humidifying the hydrogen-oxygen mixed gas filtered by the humidification filter. The pump device is connected to the water tank for generating a negative pressure in the water tank to pump back the supplementary water from the humidification device through the humidification filter and the condensate filter into the water tank and back flush the electrolyte adsorbed in the condensate filter. When the flow rate of generating the hydrogen-oxygen mixed gas by the gas generator is 600 L/hr after operating 40 to 60 hours, the loss of the electrolyte is equal to or less than 5 g.

In conclusion, the present invention is to provide a gas generator. The hydrogen-oxygen mixed gas is generated by the electrolysis device of the gas generator of the present invention. The hydrogen-oxygen mixed gas is condensed and filtered out the electrolyte through the condensate filter. The gas is humidified to reduce the amount of the electrolyte in the hydrogen-oxygen mixed gas to be inhaled by the user. In another embodiment, the gas generator can further comprise the humidification filter which is configured between the condensate filter and the humidification device for filtering out the impurities in the hydrogen-oxygen mixed gas to provide a better hydrogen-oxygen mixed gas for the user to inhale. Moreover, by replenishing the supplementary water and back flushing the electrolyte into the electrolysis device to restore the filtering function of the circulating passageway, it can not only avoid the block and corrosion in the passageway but also reduce the consumption of the electrolyte.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

The advantages, sprits, and features of the present invention will be explained and discussed with embodiments and figures as following.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
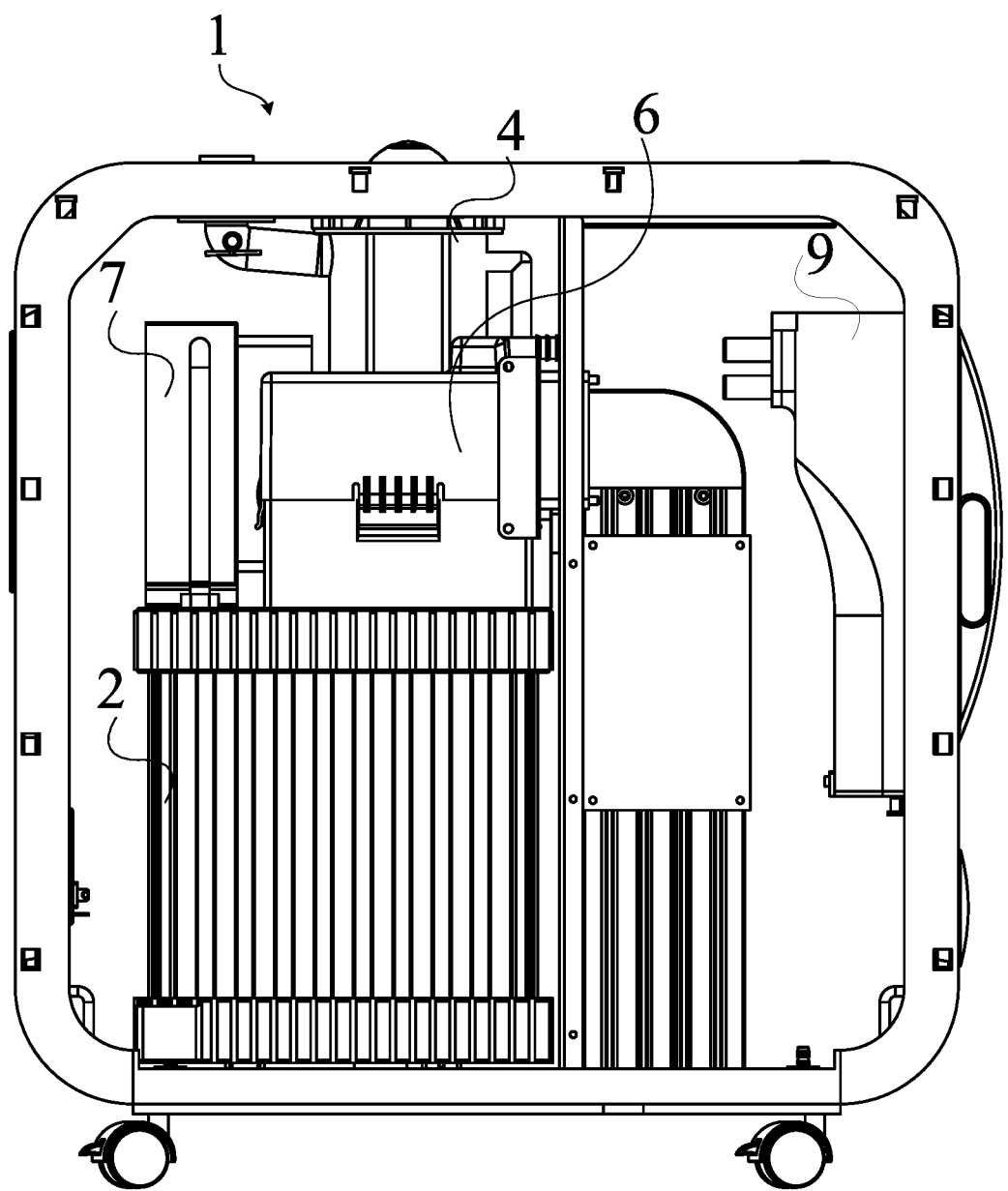
FIG. 1A and FIG. 1B are the diagrams which show a gas generator of the present invention in different angels.
Figure 1B:
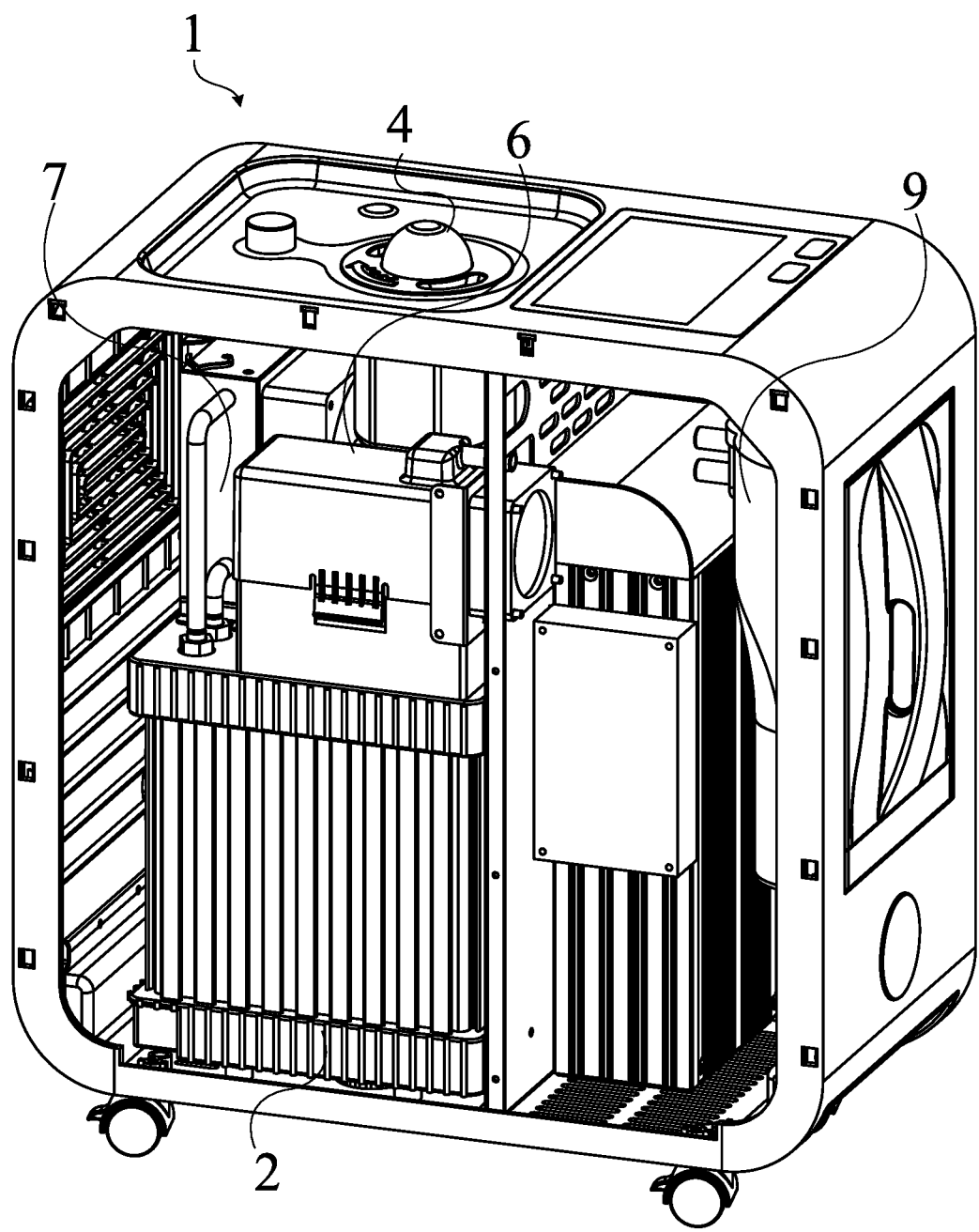
Figure 2A:
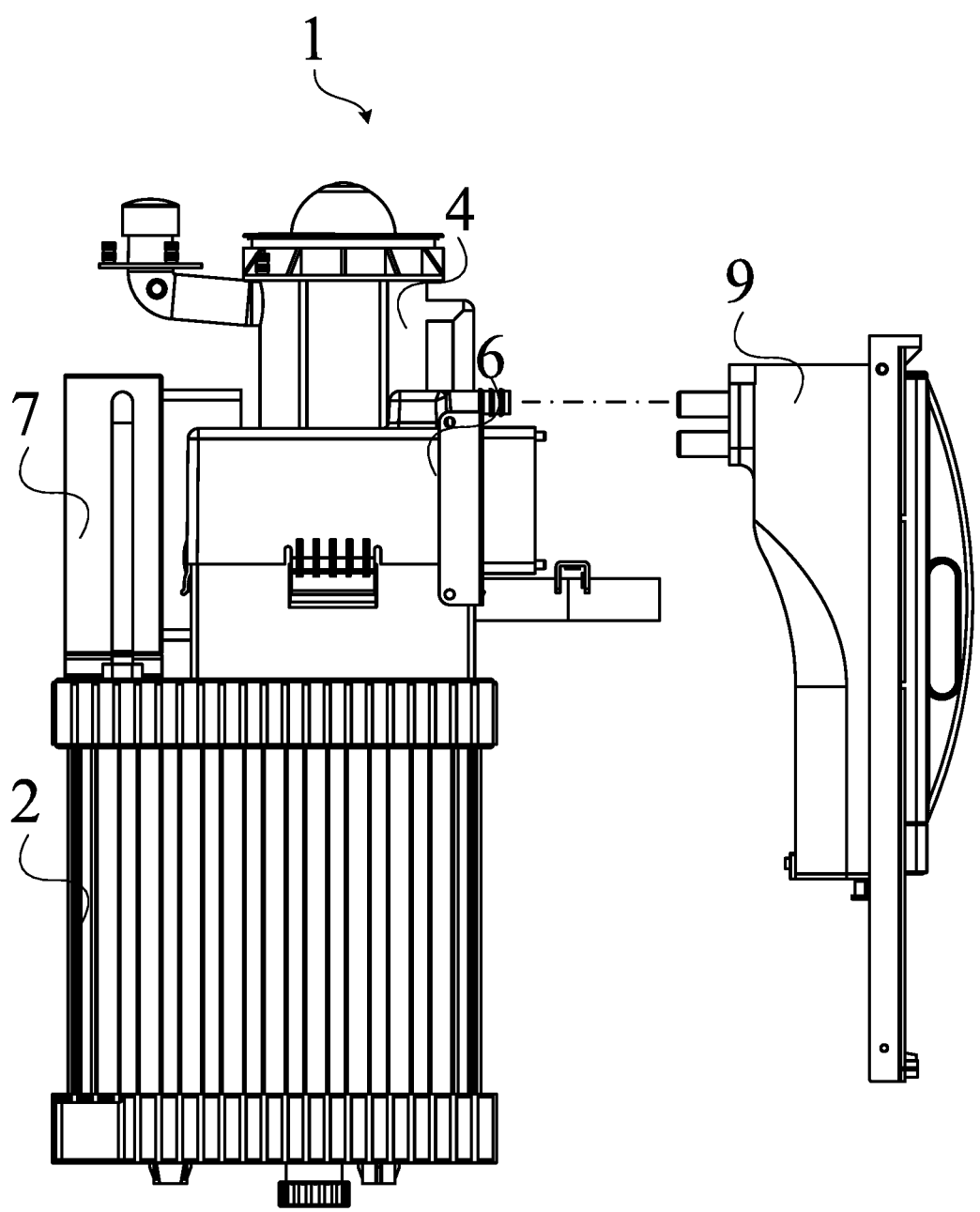
FIG. 2A, FIG. 2B and FIG. 2C are the diagrams which show the gas generator of the present invention in an embodiment in different angels.
Figure 2B:
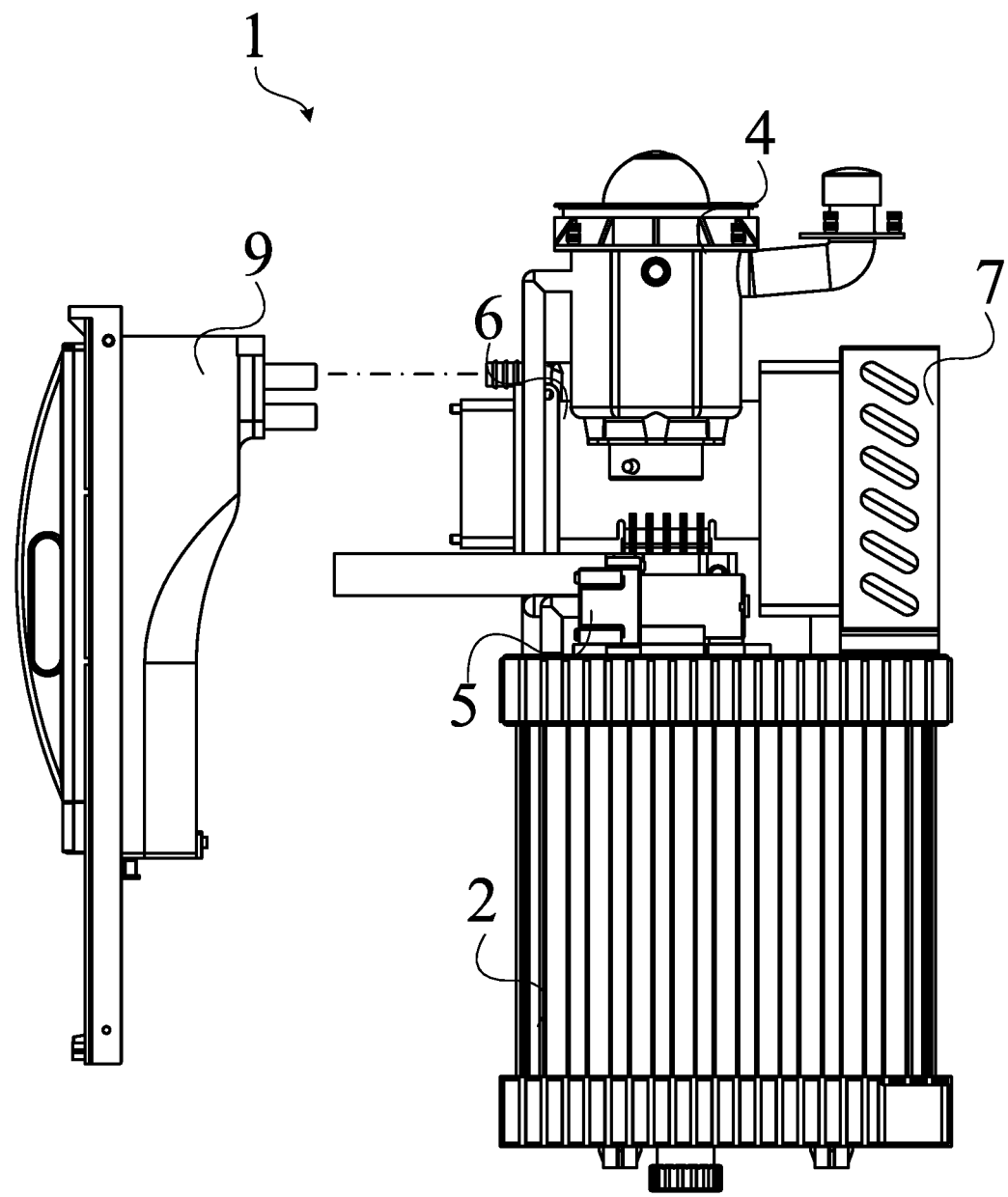
Figure 2C:
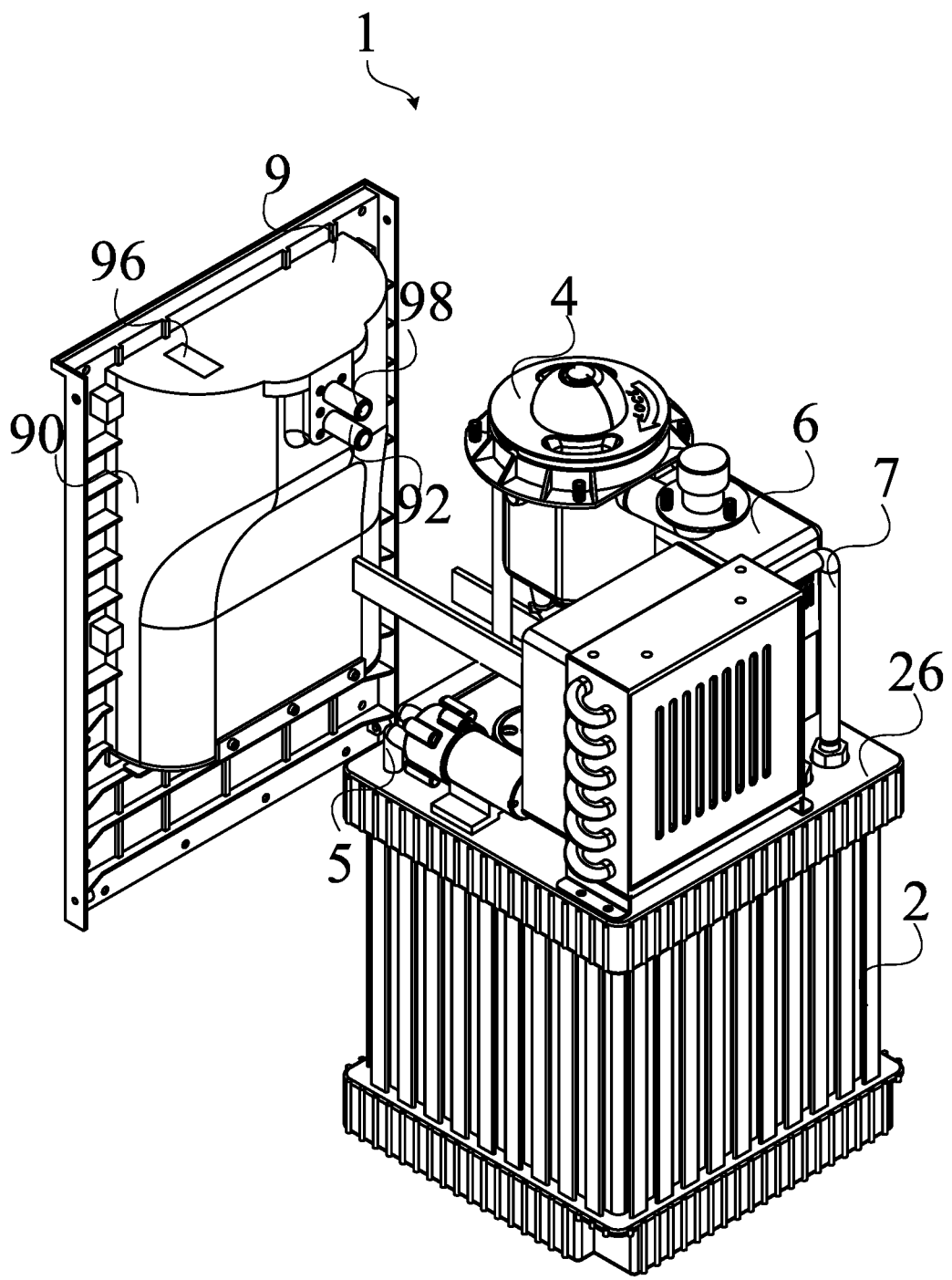
Figure 3A:
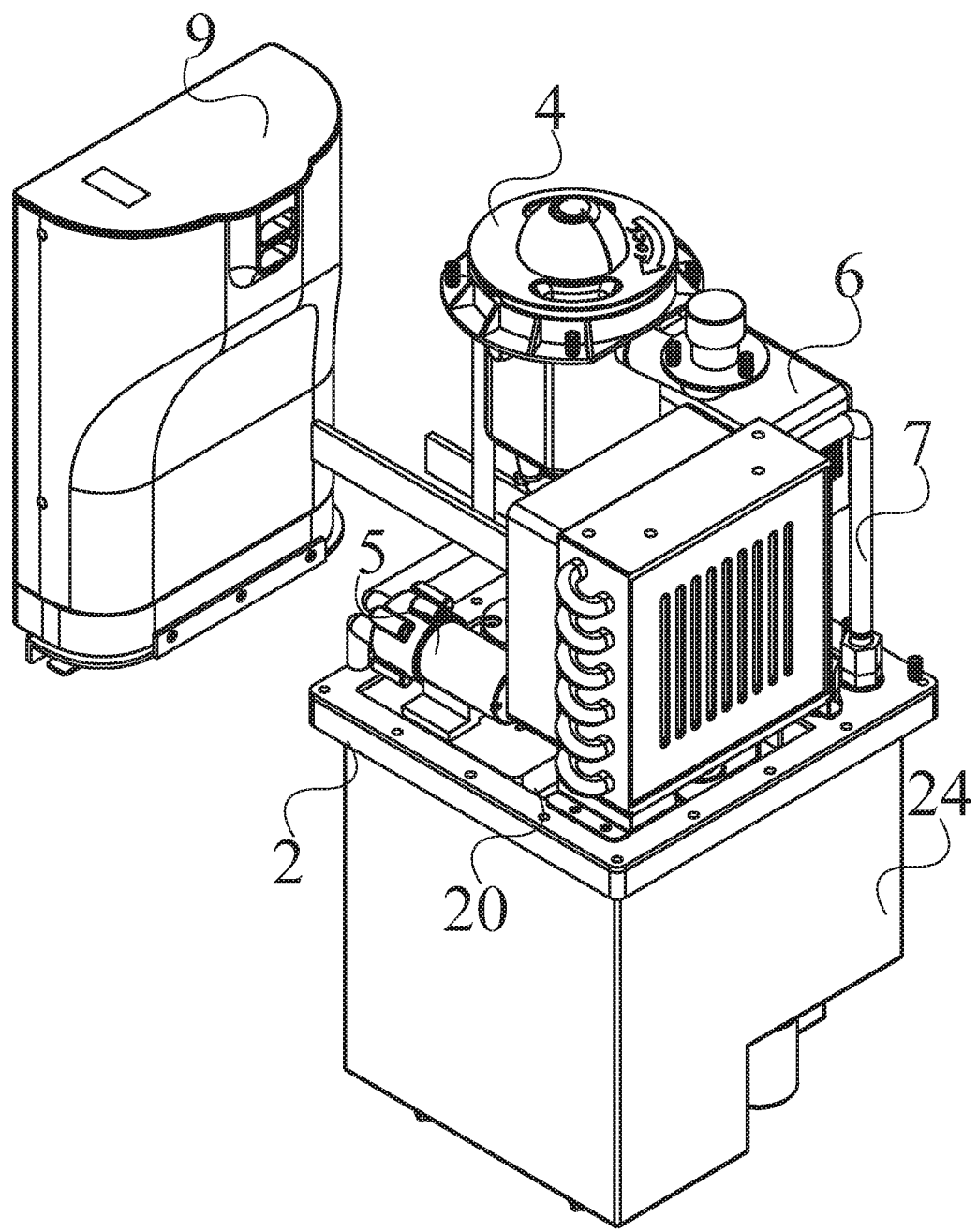
FIG. 3A, FIG. 3B and FIG. 3C are the diagrams which show the embodiment of FIG. 2A without the external shell of the water tank, the top cover of the water tank, the structure of the humidification device and the external tube of the humidification device in different angels.
Figure 3B:
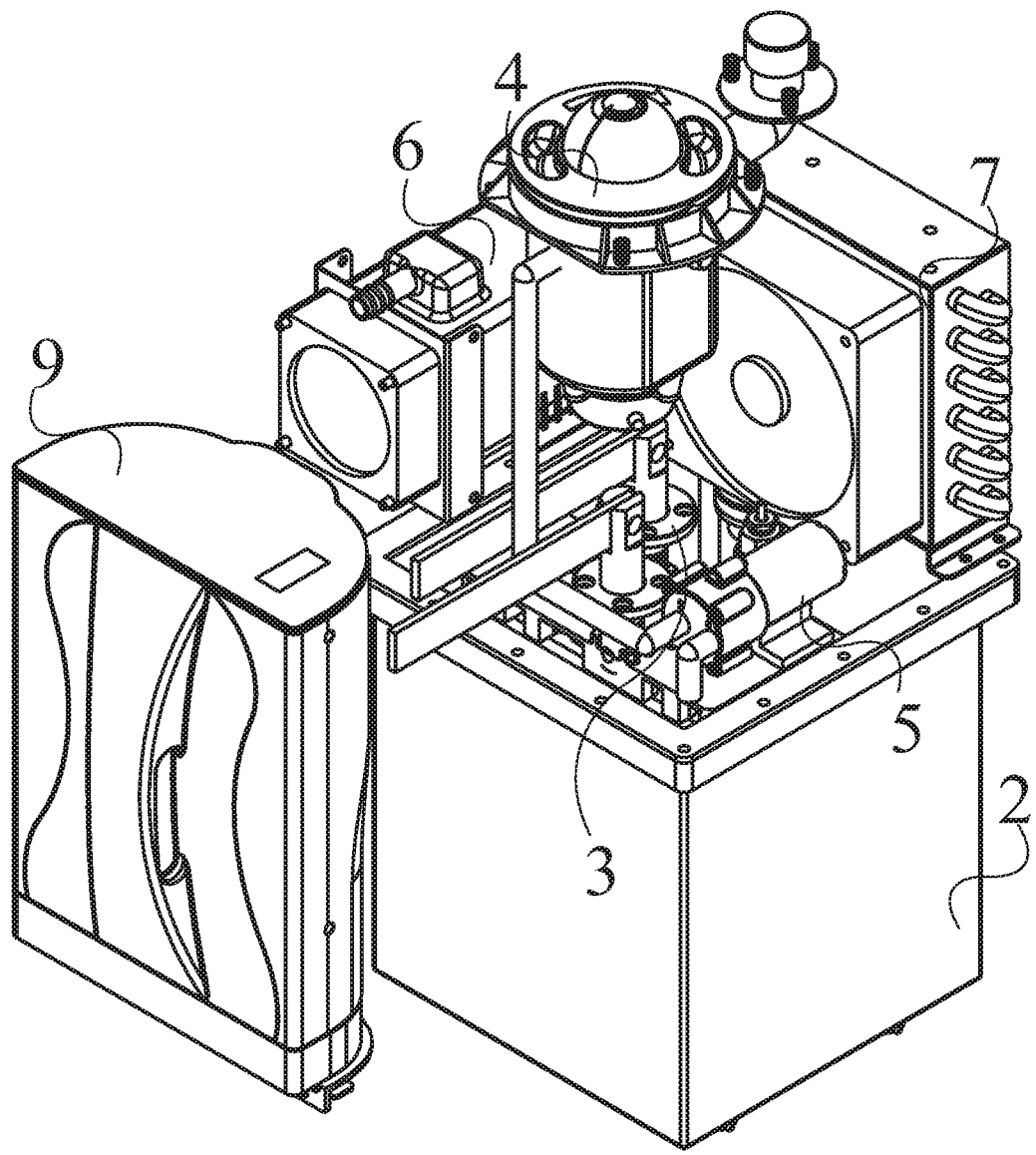
Figure 3C:
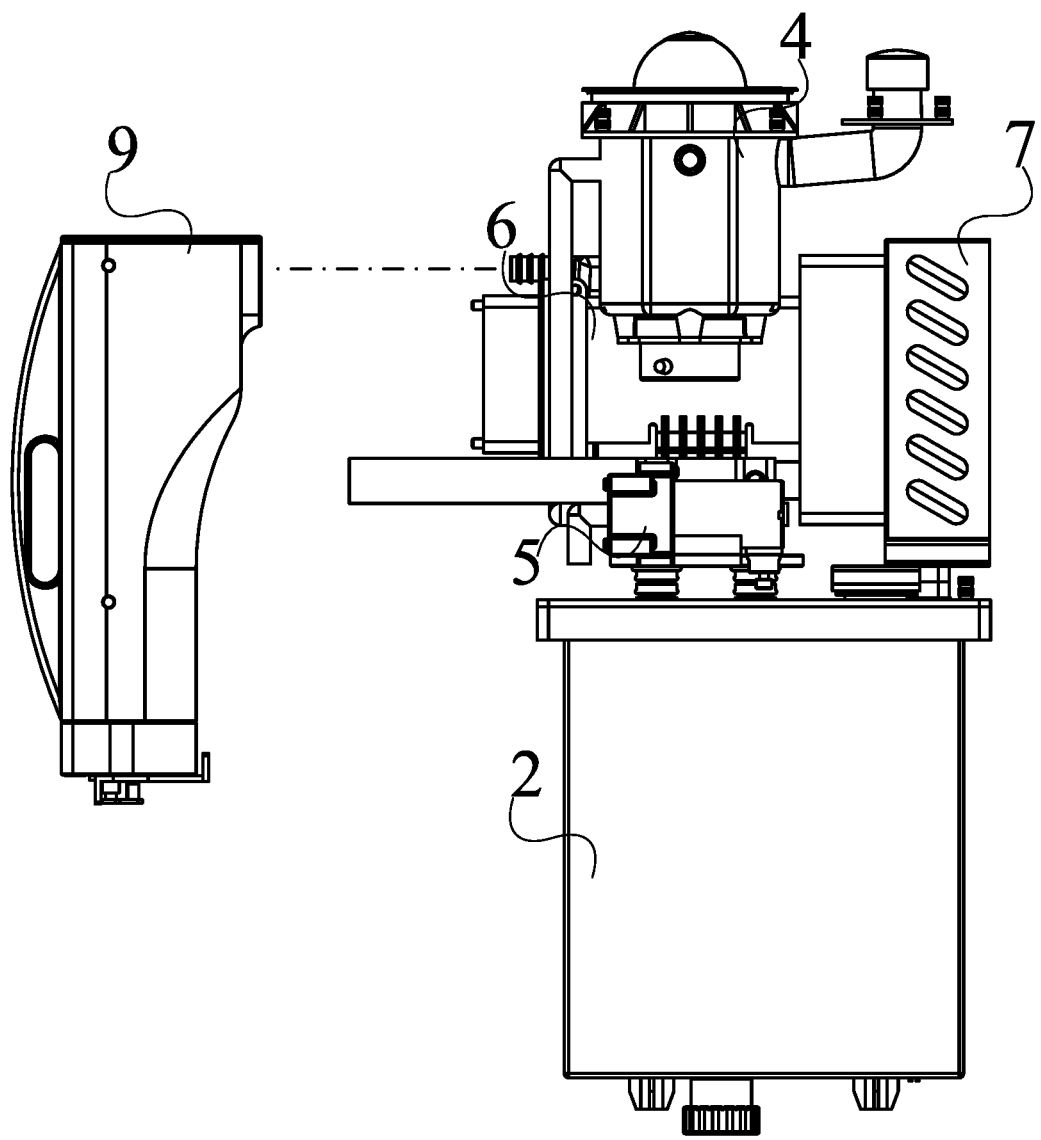

Please refer to FIG. 1A to FIG. 3C. FIG. 1A and FIG. 1B are the diagrams which show a gas generator of the present invention in different angels. FIG. 2A, FIG. 2B and FIG. 2C are the diagrams which show the gas generator of the present invention in an embodiment in different angels. FIG. 3A, FIG. 3B and FIG. 3C are the diagrams which show the embodiment of FIG. 2A without the external shell of the water tank, the top cover of the water tank, the structure of the humidification device and the external tube of the humidification device in different angels. The gas generator 1 of the present invention comprises the water tank 2, the electrolysis device 3 which is not shown in FIG. 1A and FIG. 1B but in the FIG. 4A and FIG. 4B, the atomized gas mixing tank 4, the pump device 5 which is not shown in FIG. 1A and FIG. 1B but in FIG. 2B and FIG. 4B, the condensate filter 6, the cooling device 7 and the humidification device 9.

The water tank 2 accommodates electrolyzed water, wherein the electrolyzed water comprises an electrolyte. The electrolysis device 3 is coupled to the water tank 2 for electrolyzing the electrolyzed water to generate a hydrogen-oxygen mixed gas. The condensate filter 6 is connected to the electrolysis device 3 for receiving and condensing the hydrogen-oxygen mixed gas generated by the electrolysis device 3. Then, the condensate filter filters the electrolyte in the hydrogen-oxygen mixed gas to generate the filtered hydrogen-oxygen mixed gas. The humidification device 9 receives and humidifies the filtered hydrogen-oxygen mixed gas. The humidification device 9 accommodates the supplementary water and is connected to the first hollow portion 20 of the water tank 2. The pump device 5 is connected to the first hollow portion 20 of the water tank 2. When the pump device is in operation, the gas in the first hollow portion 20 of the water tank 2 is pumped out by the pump device 5 for generating a negative pressure in the water tank 2. The humidification device 9 back flush the supplementary water into the condensate filter 6 and fills the supplementary water into the water tank 2 by the negative pressure to reduces the loss of the electrolyte. Wherein the flow rate of the hydrogen-oxygen mixed gas is 120 L/hr and the loss of the electrolyte is less than 50 g for 2000 to 3000 hours in operation. That is to say, it is expected that the flow rate of hydrogen-oxygen mixed gas generated by the gas generator is 600 L/hr and the loss of the electrolyte is equal to or less than 5 g for 40 to 60 hours in operation. The cooling device 7 is set on the cover of the water tank 2 and connected to the water tank for cooling the electrolyzed water which generates the hydrogen-oxygen mixed gas. The sentences below illustrate every design of every element of the present invention.

Figure 4A:
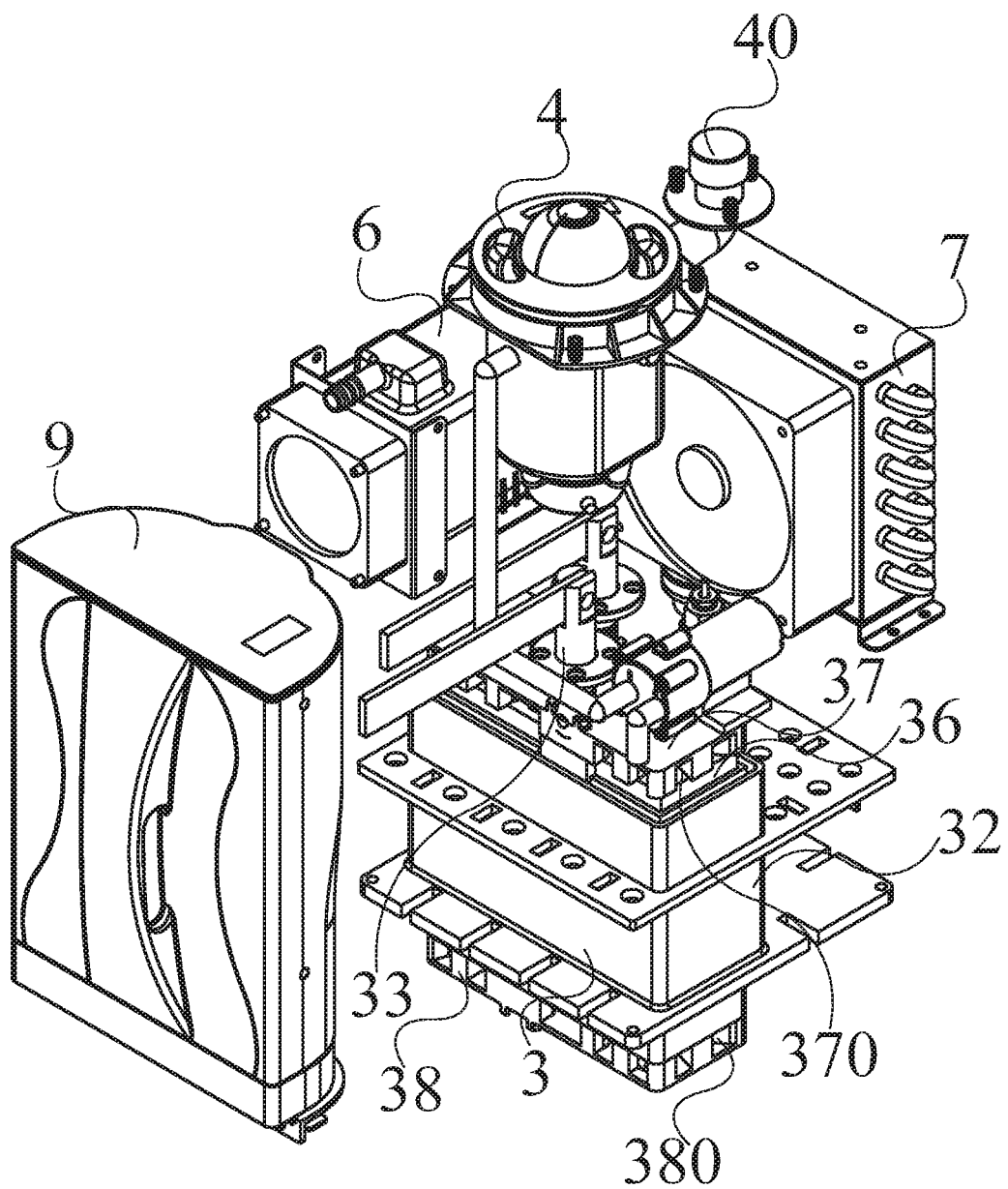
FIG. 4A and FIG. 4B are the diagrams which show the embodiment of FIG. 3A without the water tank in the different angels.
Figure 5A:
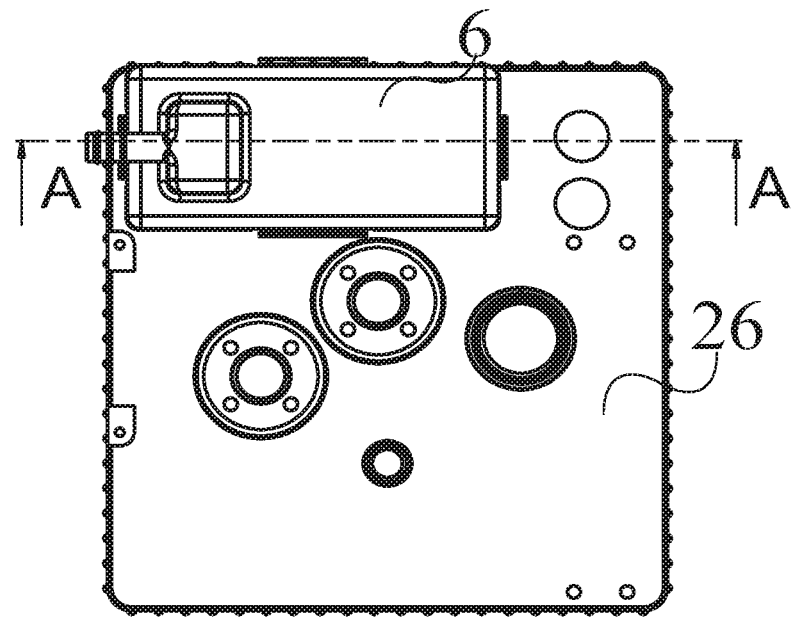
FIG. 5A and FIG. 5B are the plan view and the sectional view through the A-A line which show the embodiment of FIG. 2A only with the condensate filter and the cover of the water tank.
Figure 5B:
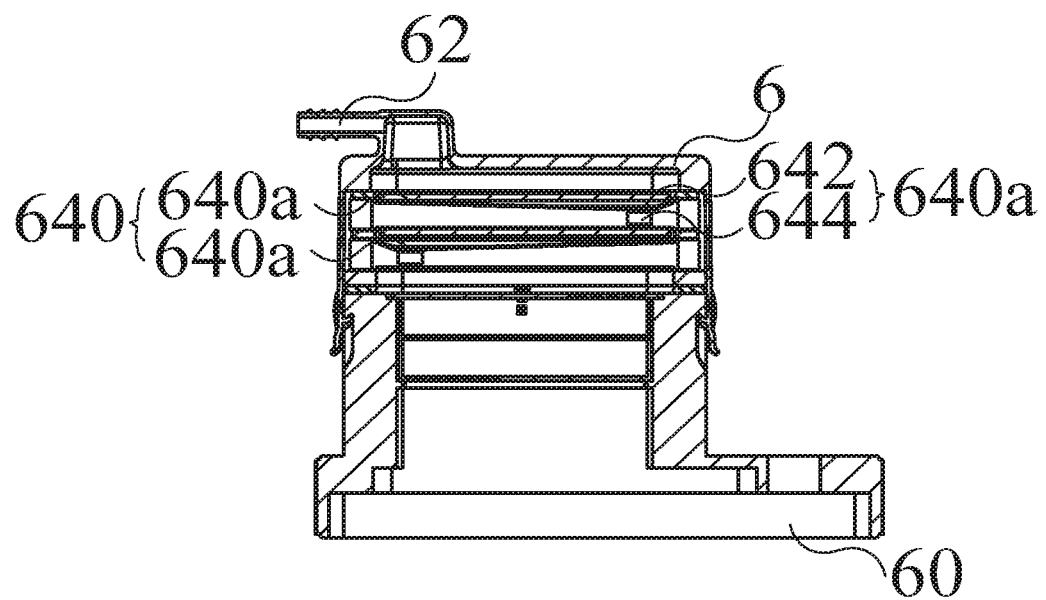
Figure 6A:
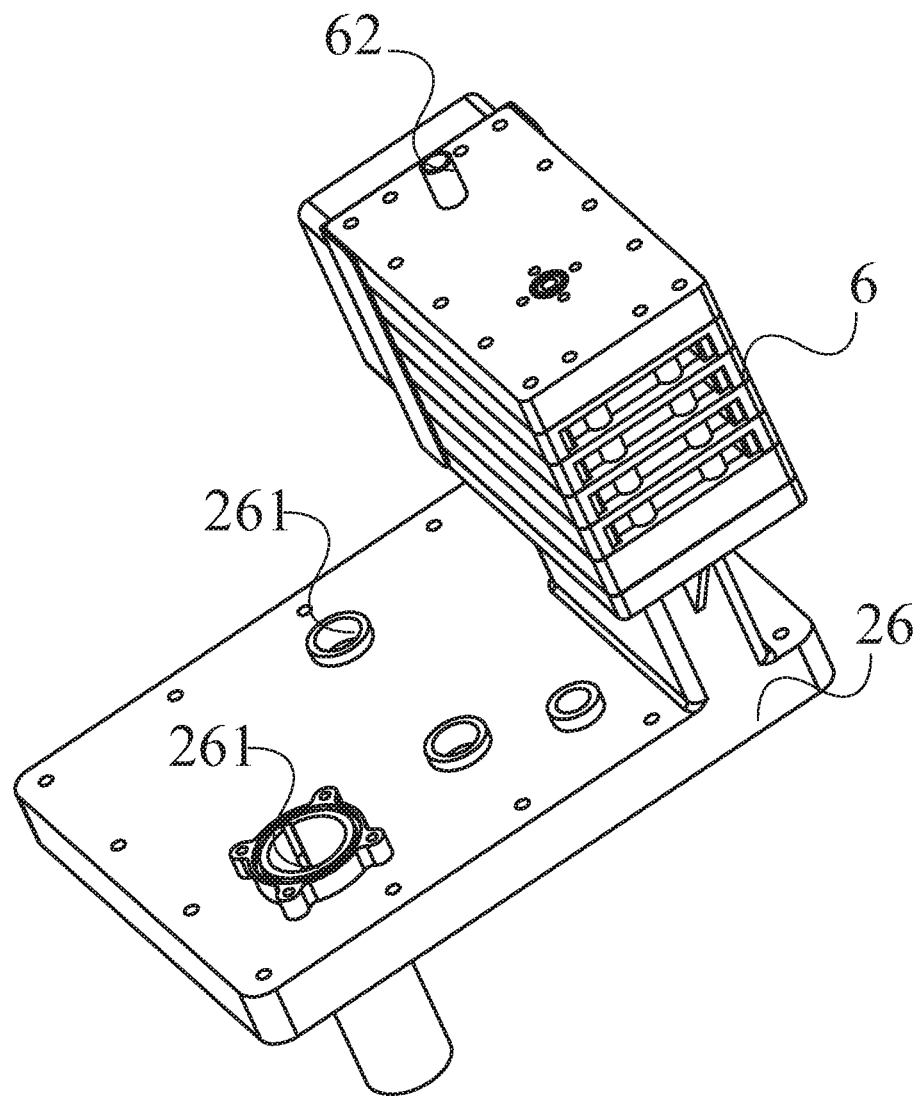
FIG. 6A and FIG. 6B are the diagrams which show the gas generator of the present invention in another embodiment only with the combination of the condensate filter and the cover of the water tank in different angels.
Figure 6B:
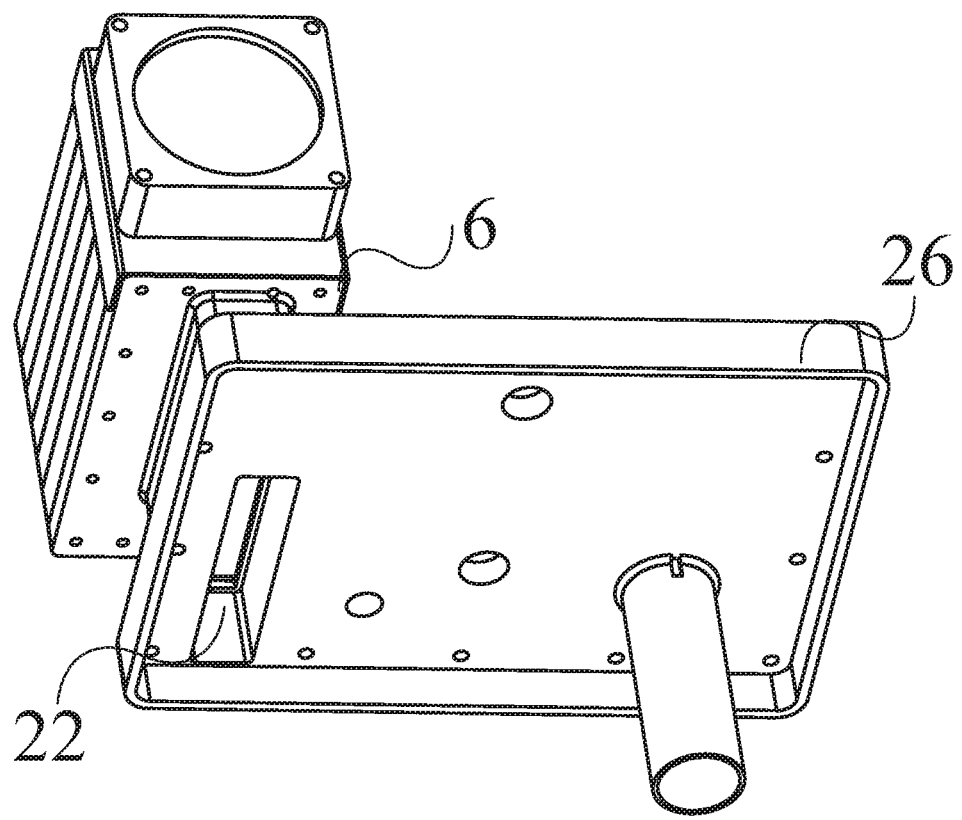

Please refer to FIG. 5A and FIG. 5B; FIG. 5A and FIG. 5B are the plan view and the sectional view through the A-A line which show the embodiment of FIG. 2A only with the condensate filter and the cover of the water tank. FIG. 6A and FIG. 6B are the diagrams which show the gas generator of the present invention in another embodiment only with the combination of the condensate filter and the cover of the water tank in different angels. The water tank 2 comprises a first hollow portion 20. The first hollow portion 20 of the water tank 2 accommodates electrolyzed water. The electrolyzed water comprises an electrolyte. The electrolyte in this embodiment is NaOH, but in practice the electrolyte is not limited to it. In practice, the electrolyte can be CaCO3, NaCl or edible NaOH. The water tank 2 further comprises a tube 22, a water tank 24 and a cover of the water tank 26. The inner space of the water tank 24 is the first hollow portion 20. The tube 22 can be set on the cover of the water tank 26 for being connected to the condensate filter 6 and the water tank 2 for outputting the hydrogen-oxygen mixed gas generated by the electrolysis device 3 and pumping the electrolyzed water into water tank 2. The cover of the water tank 26 comprises a plurality of the cover holes which are connected to the first hollow portion 20 of the water tank 2 for the electrode columns 33 of the electrolysis device 3 (shown in FIG. 4A) to be configured in by penetrating through the cover holes. Besides, the plurality of the cover holes are also available for detecting devices, such as flow rate detector, water level gauge and security valve to be configured in by penetrating through the cover holes.

Figure 4B:
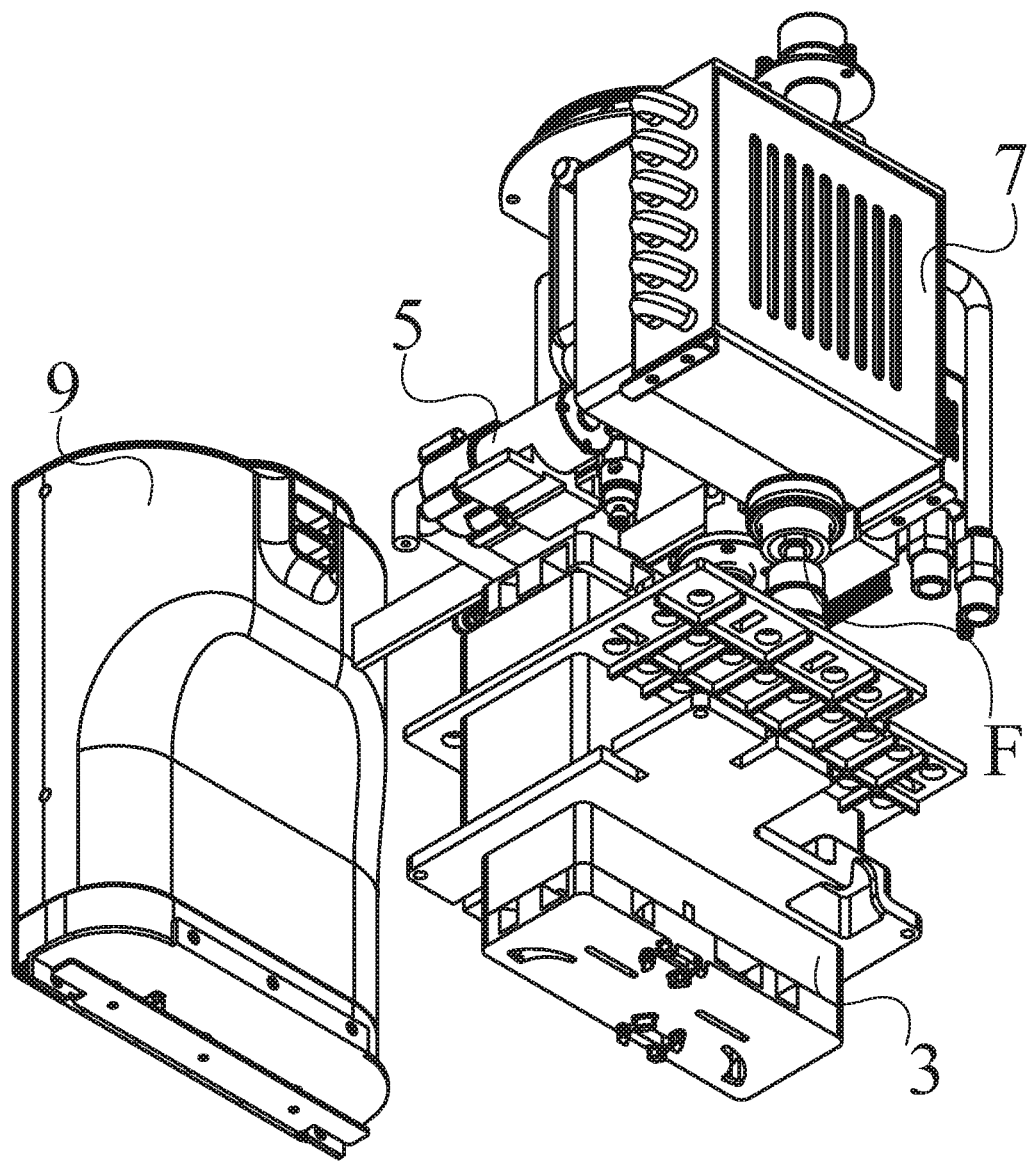

Please refer to FIG. 4A and FIG. 4B; FIG. 4A and FIG. 4B are the diagrams which show the embodiment of FIG. 3A without the water tank in the different angels. The electrolysis device 3 comprises an electrolyze tank 32, a plurality of electrodes which are not shown in the figures, the backing board 36, the upper cover 37 and the lower cover 38. Wherein the plurality of electrodes is able to be set separately in the electrolyze tank 32 to form a passageway with the plurality of electrodes. The bottom of the electrolyze tank has a plurality of lower holes. The backing board 36 is set on the upper surface of the every electrode. The backing board has a plurality of upper holes. The upper cover 37 is set on the backing board 36 corresponding to another side of the electrolyze tank 32. The upper cover 37 is able to comprise at least a first passageway 370. The pluralities of upper holes of backing board 36 are connected to the first hollow portion 20 by at least a first passageway 370 of the upper cover 37. The lower cover 38 is set on the lower surface of the electrolyze tank 32 corresponding to another side of the upper cover 37. The lower cover 38 comprises at least a second passageway 380. The plurality of lower holes set on the bottom of the electrolyze tank 32 are connected to the first hollow portion 20 by at least a second passageway 380 of the lower cover 38.

Figure 7:
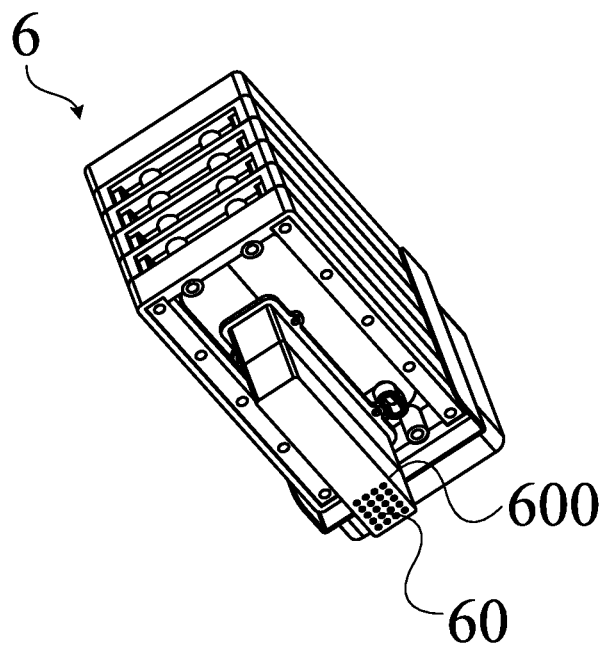
FIG. 7 is a diagram shows the combination of the condensate filter and the cover of the water tank shown in FIG. 6 without the cover of the water tank.
Figure 8:
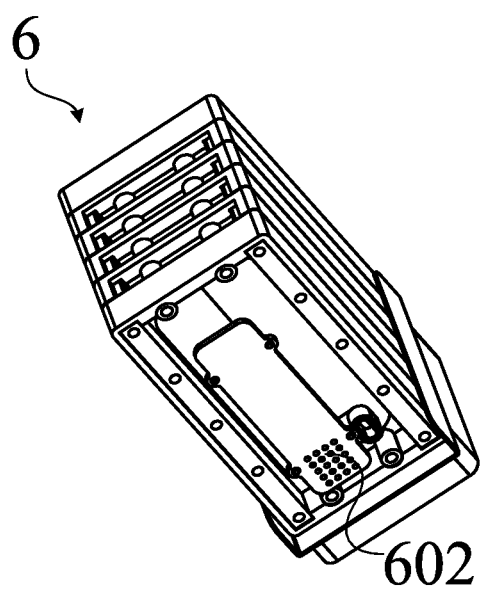
FIG. 8 is a diagram shows the combination of the condensate filter and the cover of the water tank shown in FIG. 6 without the cover of the water tank in FIG. 7 without the filter net.
Figure 9:
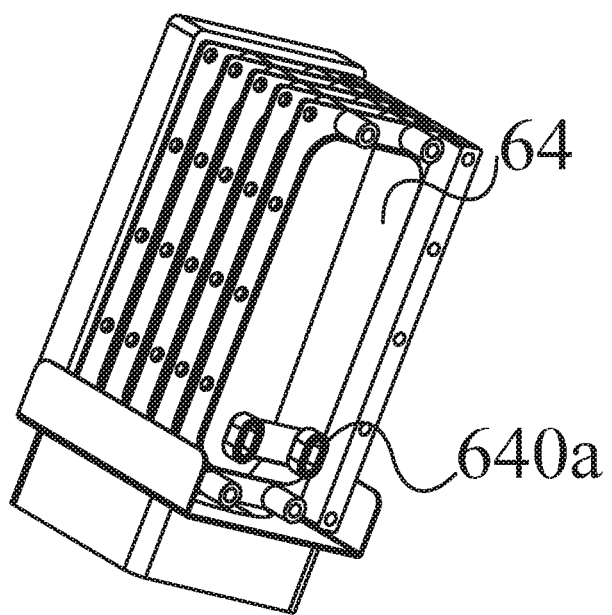
FIG. 9 is a diagram shows the combination of the condensate filter and the cover of the water tank shown in FIG. 6 without the cover of the water tank in FIG. 7 without the filter net in FIG. 8 without the filter net cover.
Figure 10A:
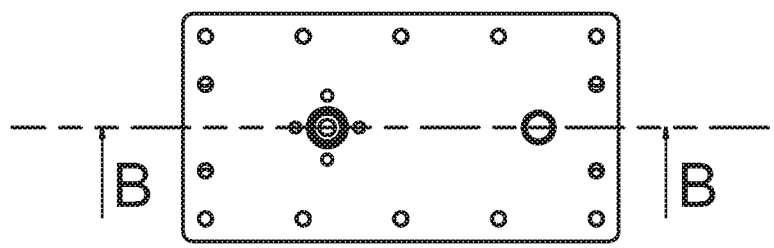
FIG. 10A and FIG. 10B are the plan view and the sectional view through the B-B line which show the condensate filter of the gas generator of FIG. 6A.
Figure 10B:
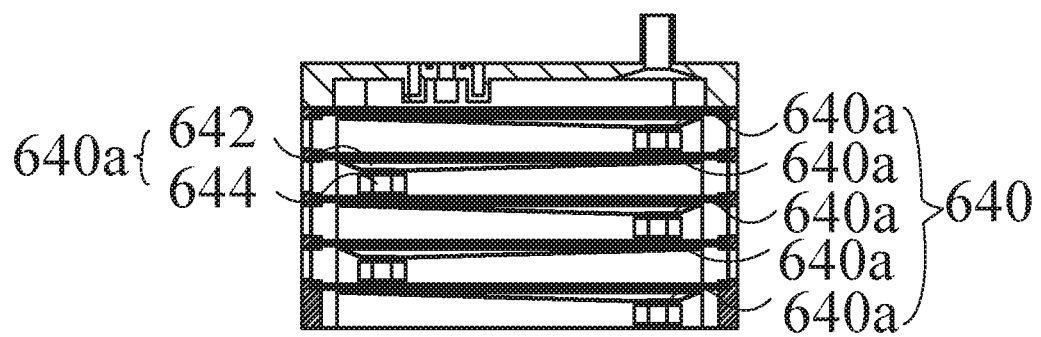

Please refer to FIG. 5A to FIG. 10B; FIG. 7 is a diagram shows the combination of the condensate filter and the cover of the water tank shown in FIG. 6 without the cover of the water tank. FIG. 8 is a diagram shows the combination of the condensate filter and the cover of the water tank shown in FIG. 6 without the cover of the water tank in FIG. 7 without the filter net. FIG. 9 is a diagram shows the combination of the condensate filter and the cover of the water tank shown in FIG. 6 without the cover of the water tank in FIG. 7 without the filter net in FIG. 8 without the filter net cover. FIG. 10A and FIG. 10B are the plan view and the sectional view through the B-B line which show the condensate filter of the gas generator of FIG. 6A. The condensate filter 6 comprises a gas inlet hole 60 and a gas outlet hole 62. The gas inlet hole 60 can be connected to the electrolysis device 3 for receiving the hydrogen-oxygen mixed gas. The gas outlet hole 62 can output the filtered hydrogen-oxygen mixed gas. Moreover, the condensate filter 6 comprises a plurality of condensate plate 64. Every condensate plate 64 comprises a passageway 640a. The passageway 640a of the condensate plate 64 is connected to the passageway 640a of the adjacent condensate plate 64 to form a circulating passageway 640 for circulating the hydrogen-oxygen mixed gas and condensing the hydrogen-oxygen mixed gas. The gas inlet hole 60 is connected to the gas outlet hole 62 by the circulating passageway 640.

In one embodiment, the passageway 640a of the condensate plate 64 is a combination of a diverging passageway 642 and a connecting passageway 644. Please refer to FIG. 5B and FIG. 10B. The diverging passageway 642 is a passageway has the diverging cross section which is not limited to the diverging passageway 642 shown in FIG. 5B and FIG. 10B. In practice, the shape of the cross section of the diverging passageway can be the half-circle, the triangle or the ladder shape. The diverging passageway 642 has a relatively broad terminal and a relatively narrow terminal. The relatively broad terminal and the relatively narrow terminal of the diverging passageway 642 have an opening. The connecting passageway 644 comprises a passageway and two corresponding openings. The two corresponding openings of the connecting passageway 644 can be connected to each other by the passageway. In one embodiment, when the diverging passageway 642 is connected to the connecting passageway 644, the diverging passageway 642 is connected to the connecting passageway 644 by the relatively broad opening connected to the opening of the connecting passageway 644. The design of the structure of the passageway 640a of the condensate plate 64 makes the horizon passageway (which is the diverging passageway 642) be connected to the vertical passageway (which is the connecting passageway 644). The horizon passageway is not limited to the passageway with diverging cross section. In practice, the horizon passageway can be the same cross section of the passageway. Moreover, when the passageway 640a of the condensate plat 64 is connected to the passageway 640a of the adjacent condensate plate 64, the two passageways 640a are connected by the relatively narrow opening of the diverging passageway 642 with the opening of the connecting passageway 644 of the adjacent condensate plate 64. Therefore, the design of the structure of the passageway 640a of the condensate plate 64 makes the passageway 640a of the condensate plate 64 be connected to the passageway 640a of the adjacent condensate plate 64 to form a circulating passageway 640 for circulating the hydrogen-oxygen mixed gas. That is to say, in the embodiment, the connecting method of the condensate plate and the adjacent condensate plate enables the hydrogen-oxygen mixed gas pass through a longer condensation-filtering route to get a better efficient of condensing and filtering. Moreover, in one embodiment, an activated carbon fiber is coupled to the passageway 640a for filtering the electrolyte in the hydrogen-oxygen mixed gas. The filter material comprising the ceramics, the quartz, the diatomaceous earth, the meerschaum or any combinations thereof is coupled to the passageway 640a. The filter material further filters the electrolyte in the hydrogen-oxygen mixed gas. Besides, in one embodiment, the gas inlet hole 60 of the present invention comprises a filter net 600 and a filter net cover 602. The filter net 600 is connected to the filter net cover 602 at the electrolysis device 3 for receiving and filtering the hydrogen-oxygen mixed gas.

In one embodiment, the circulating passageway 640 can achieve the condensing effect by the two sets of passageways 640a, which simplifies the design of the condensate filter 6 and reduces the cost. However, the invention is not limited thereto and the amount of the passageways can be adjusted according to the design requirement.

Figure 11:
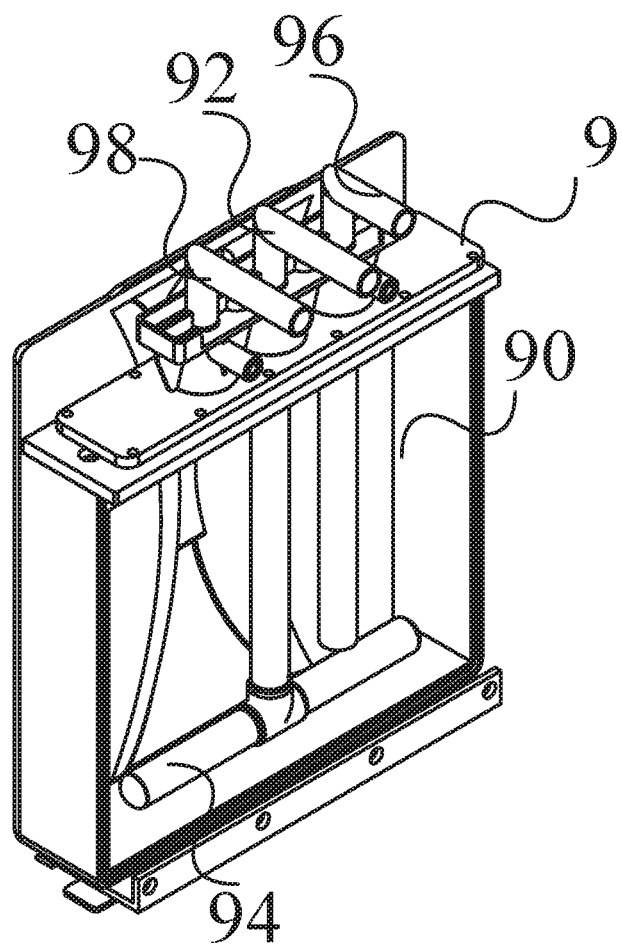
FIG. 11 is the diagram which shows the humidification device of the gas generator of the present invention in another embodiment.

Please refer to FIG. 2C and FIG. 11. FIG. 11 shows the humidification device of the gas generator of the present invention in another embodiment. The humidification device 9 comprises a hollow main body 90, a first tube 92, at least an output tube 94, a third tube 96, and a fourth tube 98. The hollow main body 90 can accommodate supplementary water. The second tube 92 is set on the hollow main body 90 for connecting the electrolysis device 3. At lease an output tube 94 is coupled to the hollow main body 90 and connected to the second tube 92. The second tube 92 is connected to two output tubes 94 to form a T-shape. In practice, the present invention is not limited thereto, and the connection of the second tube to at least one output tube 94 can be adjusted according to the design requirement.

Moreover, the surface of two output tubes 94 comprises a plurality of holes. In one embodiment, the diameter of the holes ranges from 2 nm to 3 nm for refining the gas to form easily-dissolved fine bubbles. In practice, the invention is not limited thereto, and the diameter of the holes is adjustable according to the requirement of the user. Two rubber plugs are respectively set on the terminal of two output tubes 94 connected to the second tube 92 for outputting the hydrogen-oxygen mixed gas in the second tube 92 by the pluralities of nano-holes on the output tube 94 into the hollow main body 90. In practice, the present invention is not limited thereto, and the terminal of two output tubes 94 connected to the second tube 92 can be designed as closed face.

The third tube 96 can be set on the hollow main body 90 for replenishing the supplementary water W2. In practice, the third tube can be connected to a pilot hole. The hydrogen water is output through the pilot hole by the third tube or input into the supplementary water. The fourth tube 98 can be set on the hollow main body 90 for outputting the humidified hydrogen-oxygen mixed gas.

Please refer to FIG. 3B and FIG. 4A. The pump device 5 can be set on the water tank cover 26 and be connected to the first hollow portion 20 of the water tank 2 for taking out the gas in the water tank 2 to generate a negative pressure to input the supplementary water from the humidification device 9 to the water tank and back flush the electrolyte in the condensate filter 6 into the first hollow portion 20 of the water tank 2.

Please refer to FIG. 3B and FIG. 4. The atomized gas mixing tank 4 can be connected to the humidification device 9 for receiving the humidified hydrogen-oxygen mixed gas. The atomized gas mixing tank can generate the atomized gas, wherein the atomized gas comprises at least one of the water vapor, the atomized liquid, the volatile purified oils and combinations thereof. The atomized gas mixing tank can mix the atomized gas and the humidified hydrogen-oxygen mixed gas to form the healthy gas for user to inhale. Furthermore, the atomized gas mixing tank 4 can comprise a gas outlet 40. The design of the gas outlet is not limited to the diagram shown in FIG. 4A in practice. The gas outlet can be the gas outlet tube, and the gas outlet is according to the requirement of the user. The gas outlet 40 of the atomized gas mixing tank 4 and the pump device 5 is connected to each other. In one embodiment, when the electrolysis device 3 stops electrolyzing electrolyzed water for generating the hydrogen-oxygen mixed gas, the pump device starts to operate. The pump device 5 pumps out the gas in the water tank and output the gas from the gas outlet 40 of the atomized gas mixing tank 4 to generate a negative pressure in the water tank to input the supplementary water from the humidification device into the water tank and back flush the electrolyte absorbed in the condensate filter into the water tank.

The sentences mentioned above elaborate every design of every element; hereafter, the sentences mentioned below elaborate every method of combination and every application.

In the electrolysis device 3, there are a plurality of electrodes set on the electrolyze tank 32, the backing board 36 is set on the surface of every electrode, the upper cover 37 is covered on another terminal of backing board 36 corresponding to the electrolyze tank 32, and the lower cover 38 is covered on the lower surface of the electrolyze tank 32 corresponding to another terminal of the upper cover 37.

In the water tank 2 and the electrolysis device 3, the anode plate and the cathode plate of the electrolysis device 3 are respectively fixed on the water tank cover 26 by two electrode columns 33. When the water tank 24 combined with the water tank cover 26, the electrolysis device 3 can be fixed and hung in the water tank 2. Wherein, the water tank 2 and the electrolysis device 3 are connected to each other. The detecting device, such as the flow rate detector F, is penetrated through the plurality of cover holes 261 and configured on the water tank cover 26.

In the water tank 2, the electrolysis device 3 and the condensate filter 6, the water tank 2 which has electrolysis device 3 is connected to the condensate filter 6 by the tube 22 of the water tank 2 and the gas inlet hole 60 of the condensate filter 6. Then, the condensate filter 6 which is connected to the water tank is connected to the humidification device 9 by the connection between the gas outlet hole 60 of the condensate filter 6 and the second tube 92 of the humidification device 9. Moreover, the atomized gas mixing tank 4 can be connected to the fourth tube 98 of the humidification device 9.

In practice, the water tank 2 accommodates an electrolyzed water W, the electrolysis device 3 is coupled to the water tank 2 for electrolyzing the electrolyzed water W to generate a hydrogen-oxygen mixed gas. The hydrogen-oxygen mixed gas generated at the passageway of the electrode is input into the first hollow portion 20 by the upper hole on the backing board 36 and the first passageway 370 of the upper cover 37. The hydrogen-oxygen mixed gas which is input into the first hollow portion 20 is output through the tube 22 of the water tank 2. The hydrogen-oxygen mixed gas output from the tube 22 of the water tank 2 is input into the condensate filter 6 through the gas inlet hole 60 of the condensate filter 6 to condense and filter. The hydrogen-oxygen mixed gas which is went through the gas inlet hole 60 of the condensate filter 6 is wen t through the filter net 600 and the filter net cover 602 first to initially filter. Then the initially filtered hydrogen-oxygen mixed gas is input into the circulating passageway 640 to do the condensation. At the same time, the hydrogen-oxygen mixed gas is filtered by the activated carbon fiber coupled to the passageway 640*a*, and the hydrogen-oxygen mixed gas makes the electrolyte be adsorbed in the circulating passageway 640*a*. Then the filtered hydrogen-oxygen mixed gas is output by the gas outlet hole 62 of the condensate filter 6.

Moreover, the filtered hydrogen-oxygen mixed gas is passed into the humidification device 9 by the second tube 92 which is connected to the gas outlet hole 62. The filtered hydrogen-oxygen mixed gas received by the second tube 92 is input into the hollow main body 90 by the pluralities of nano-holes of two output tubes 94. In practice, because there are pluralities of nano-holes on the surface of the output tube 94, the hydrogen-oxygen mixed gas in the humidification device is able to be small to form the dissolvable small gas bubbles. After the filtered hydrogen-oxygen mixed gas is humidified by the humidification device, the electrolyte in the hydrogen-oxygen mixed gas become lower for users to use safely when the electrolyte is dissolved in the water. The humidified hydrogen-oxygen mixed gas which is output by the humidification device 9 is provided for the user to inhale. In real practice, the present invention is not limited thereto, and the humidified hydrogen-oxygen mixed gas which is output by the humidification device 9 can be mixed with the atomized gas generated by the atomized gas mixing tank 4 to form a healthy gas for the user to inhale.

Moreover, when the electrolysis device 3 stops electrolyzing the electrolyzed water for generating the hydrogen-oxygen mixed gas, the pump device can pump out the gas in the water tank 2 to generate a negative pressure. The supplementary water recharged by the third tube 96 can be input from the humidification device 9 into the water tank 2 which has electrolysis device 3 by the negative pressure mentioned above. More particularly, the supplementary water is input from the humidification device 9 into the condensate filter 6 by the connection between the second tube 92 of the humidification device 9 and the gas outlet hole 62 of the condensate filter 6. Moreover, the electrolyte adsorbed in the circulating passageway 640 of the condensate filter 6 can be flushed back into the water tank 2 of the electrolysis device 3 with the supplementary water through the gas inlet hole 60 and the tube 22 for restoring the filtering function of the circulating passageway. It can not only avoid the block and corrosion in the circulating passageway 640 but also reduce the consumption of the electrolyte. In one embodiment, after the hydrogen-oxygen mixed gas generated by the gas generator generated under 120 L/hr for 2000 hours to 3000 hours, the loss of the electrolyte is equal to or less than 50 g and the present invention is not limited thereto. In practice, after the hydrogen-oxygen mixed gas generated by the gas generator has generated under 600 L/hr for 40 hours to 60 hours, the loss of the electrolyte is equal to or less than 5 g.

In practice, the present invention uses the supplementary water to back flush the electrolyte into the water tank 2 of the electrolysis device 3 for providing the electrolysis device 3 with the electrolyzed water which is used for electrolyzing. Moreover, the replenished electrolyzed water of the first hollow portion 20 needs to go through the second passageway 380 of the lower cover 38 and the pluralities of lower holes corresponding to the electrode passageway of the electrolyze tank 32 for providing electrolysis device 3 with the electrolyzed water W when the electrolysis device 3 is in operation. In one embodiment, the gas generator of the present invention can detect the water level in the first hollow portion accommodated in the water tank and/or the electrolysis device by the water level gauge to control the replenishment of the electrolyzed water.

Please refer to FIG. 4. The flow rate detector F is coupled to the electrolysis device 3 for detecting the flow rate of the hydrogen-oxygen mixed gas. In one embodiment, the flow rate of the hydrogen-oxygen mixed gas of the gas generator 1 ranges from the 0.01 L/min to the 12 L/min. After the gas generator generates the hydrogen-oxygen mixed gas generated under 120 L/hr for 2000 hours to 3000 hours, the loss of the electrolyte is equal to or lower than 50 g; and it is predictable that the loss of the electrolyte is equal to or lower than 5 g after the gas generator generates the hydrogen-oxygen mixed gas generated under 600 L/hr for 40 hours to 60 hours; or it is predictable that the loss of the electrolyte is equal to or lower than 0.25 g after the gas generator generates the hydrogen-oxygen mixed gas generated under 30 L/hr for 40 hours to 60 hours; it is also predictable that the loss of the electrolyte is equal to or lower than 2 g after the gas generator generates the hydrogen-oxygen mixed gas generated under 240 L/hr for 40 hours to 60 hours; it is also predictable that the loss of the electrolyte is equal to or lower than 3 g after the gas generator generates the hydrogen-oxygen mixed gas generated under 360 L/hr for 40 hours to 60 hours; and it is also predictable that the loss of the electrolyte is equal to or lower than 2 g after the gas generator generates the hydrogen-oxygen mixed gas generated under 30 L/hr for 40 hours to 600 hours. In practice, the present invention is not limited to it; the user can adjust the flow rate and the operation time according to the usage requirement.

Figure 12:
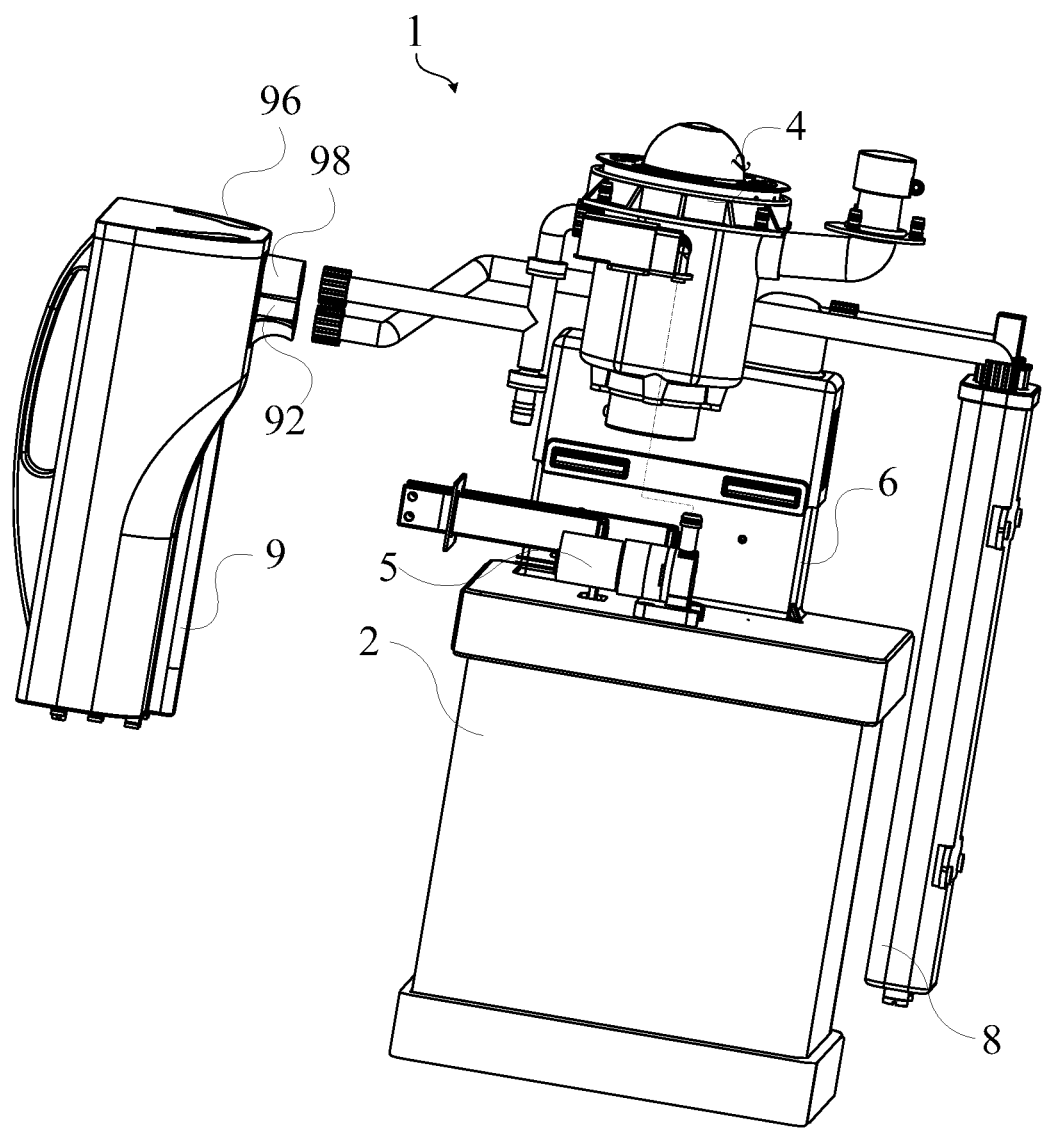
FIG. 12 is the diagram which shows the gas generator of the present invention in another embodiment.

Please refer to FIG. 12, FIG. 12 shows the gas generator of the present invention in another embodiment. In one embodiment, the gas generator 1 comprises the water tank 2, the electrolysis device 3, the condensate filter 6, the humidification filter 8, the humidification device 9 and the pump device 5. The electrolysis device 3 is coupled to the water tank 2. The condensate filter 6 is connected between the electrolysis device 3 and the humidification filter 8. The humidification filter 8 accommodates water. The humidification filter 8 is connected to the condensate filter 6. The humidification device 9 is connected to the humidification filter 8. The condensate filter condenses the hydrogen-oxygen mixed gas generated by the electrolysis device and filters the electrolyte of the hydrogen-oxygen mixed gas. The humidification filter 8 is used for filtering the filtered hydrogen-oxygen mixed gas which is filtered by the condensate filter. The humidification device 9 can humidify the hydrogen-oxygen mixed gas which is filtered by the humidification filter 8.

In one embodiment, the humidification filter 8 comprises a tank, a first tube, a first filter, and a first tube. The tank has a space for accommodating water but not limited to it. The tank is able to accommodate the liquid according the usage requirement. The first tube is connected to the external side and the inner side of the tank. The first tube has the first terminal and the second terminal corresponding to the first terminal. The first terminal and the second terminal are able to connect the external side and the inner side of the tank. The first filter is set at the second terminal of the first tube for connecting the external side and the inner side of the tank.

In one embodiment, the humidification filter 8 further comprise a second filter 23 coupled to the entrance and the exit of the first tube. In practice, the second filter can be coupled under the first tube to directly output the filtered hydrogen-oxygen mixed gas. The first filter and the second filter may be made of porous plastics. In another embodiment, the porous plastics may be a polyethylene but not limited to it.

The hydrogen-oxygen mixed gas is pumped from the outside through the first terminal of the first tube, and the hydrogen-oxygen mixed gas is pumped into the tank through the second terminal of the first tube. Because the first filter is set on the second terminal, the hydrogen-oxygen mixed gas is pumped through the first filter when the gas mixture is output from the second terminal, and the impurities is filtered out by the first filter, wherein the impurities can be electrolytes. After the hydrogen-oxygen mixed gas is pumped into the water in the tank, the hydrogen-oxygen mixed gas is filtered by the water. The filtered gas comprising hydrogen and oxygen which can pass through the second filter element to filter the vapor in the hydrogen-oxygen mixed gas and be pumped out from the tank through the first tube.

In one embodiment, the humidification filter 8 comprises a tube. One terminal of the tube is connected between the first terminal and the second terminal of the first tube. One of the terminals of branch connects the first tube and the second tube and another terminal of branch comprises a one-way valve. The one-way valve can be used to keep the hydrogen-oxygen mixed gas being output from the branch. Therefore, when the first tube receives the hydrogen-oxygen mixed gas from the outside, the hydrogen-oxygen mixed gas is blocked by the one-way valve and pumped through the first terminal of the first tube to the second terminal and into the tank. In one embodiment, the one-way valve of the humidification filter 8 can control the water level of the tank (not shown in the figures). When the water level is higher than a predetermined value, the humidification filter 8 will pump out the water in the tank by the one-way valve through the first tube and the branch until the water level is lower than the predetermined value in order to maintain the water level of the tank.

The pump device is connected to the water tank for generating negative pressure in the water tank in order to pump back the supplementary water from the humidification device through the condensate filter into the water tank, and the electrolyte adsorbed in the condensate filter is back flushed to the water tank. When the flow rate of generating the hydrogen-oxygen mixed gas by the gas generator is 600 L/hr after operating 40 to 60 hours, the loss of the electrolyte is less than 5 g.

In one embodiment, the electrolysis device is connected to the external power source. The output voltage of the power source ranges from 17V to 27V. The output electric current of the power source ranges from 30 A to 40 A. That is to say, the amount of the output gas of the electrolysis device ranges from 1.5 L/min to 4.0 L/min. The voltage of every pair of electrodes ranges from 1.5V to 3V. If there are eight pairs of electrodes, the voltage ranges from 12V to 24V but the voltage is not limited to it. In practice, when the electrolysis device is connected to the external power source, the output voltage of the power source ranges from 5V to 24V, the output electric current ranges from 2 A to 150 A, and the power of the electrolysis device ranges from 10 W to 3600 W, the output gas generated by the electrolysis device ranges from 0.01 L/min to 12 L/min.

In conclusion, the hydrogen-oxygen mixed gas is generated by the electrolysis device of the gas generator of the present invention. The electrolyte in the hydrogen-oxygen mixed gas is able to be condensed and filtered out by the condensate filter. The amount of the electrolyte in the hydrogen-oxygen mixed gas is reduced after being humidified by the humidification device for the user to inhale. In another embodiment, the gas generator further comprises a humidification filter configured between the condensate filter and the humidification device which is able to filter out the impurities in the hydrogen-oxygen mixed gas for providing a better hydrogen-oxygen mixed gas for the user to inhale. Besides, the supplementary water is pumped back into the water tank through the humidification device by the pump device which is connected to the water tank. Furthermore, the gas generator pumps the supplementary water and back flushes the electrolyte into the electrolysis device to restore the filtering function of the circulating passageway. Therefore, the present invention not only avoid the blocking, etching, and corrosion in the circulating passageway but also reduce the consumption of the electrolyte.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator comprising:
   a water tank accommodating electrolyzed water;
   an electrolysis device having a case disposed within the water tank, the electrolysis device configured to electrolyze the electrolyzed water to generate a hydrogen-oxygen mixed gas;
   a condensate filter coupled to the electrolysis device for receiving and filtering electrolyte in the hydrogen-oxygen mixed gas to generate a filtered hydrogen-oxygen mixed gas, wherein a gas outlet hole of the condensate filter is configured to output the filtered hydrogen-oxygen mixed gas, and the gas outlet hole of the condensate filter is configured to receive a supplementary water to flush the filtered electrolyte out of the condensate filter;
   a humidification device accommodating the supplementary water and coupled to the condensate filter for humidifying the filtered hydrogen-oxygen mixed gas to generate a humidified hydrogen-oxygen mixed gas, wherein the humidification device further comprises at least an output tube having a plurality of holes, and the filtered hydrogen-oxygen mixed gas is received by the humidification device and outputted through the plurality of holes of the output tube to generate the humidified hydrogen-oxygen mixed gas; and
   a pump device configured to drive the supplementary water from the humidification device through the condensate filter to the water tank, such that the filtered electrolyte is flushed out of the condensate filter.

2. The gas generator of claim 1, wherein the electrolysis device comprises a plurality of electrodes set inside the case.

3. The gas generator of claim 1, further comprising anatomized gas mixing tank coupled to the humidification device to receive the humidified hydrogen-oxygen mixed gas, the atomized gas mixing tank generating an atomized gas and mixing the atomized gas with the humidified hydrogen-oxygen mixed gas to form a healthy gas, wherein the atomized gas comprises water vapor, atomized liquid, volatile purified oil, or combinations thereof.

4. The gas generator of claim 1, wherein the condensate filter comprises a plurality of condensate plates, and each condensate plate has a passageway, each passageway of the condensate plate is connected to the passageway of the adjacent condensate plate to form a circulating passageway for circulating the hydrogen-oxygen mixed gas.

5. The gas generator of claim 4, wherein each passageway of the condensate plate is disposed with an activated carbon fiber for filtering out the electrolyte in the hydrogen-oxygen mixed gas, each activated carbon fiber is separated from the other.

6. The gas generator of claim 4, wherein each passageway of the condensate plate is disposed with a filter material, each filter material is separated from the other, and the filter material comprises ceramics, quartz, diatomaceous earth, meerschaum or combinations thereof.

7. The gas generator of claim 1 further comprising a cooling device coupled to the water tank for cooling the electrolyzed water.

8. A gas generator, comprising:
a an electrolysis device configured for electrolyzing electrolyzed water to generate a hydrogen-oxygen mixed gas;
a condensate filter vertically spaced apart from the electrolysis device and configured for filtering electrolyte in the hydrogen-oxygen mixed gas to generate a filtered hydrogen-oxygen mixed gas and a filtered electrolyte; and
a humidification device accommodating a supplementary water and humidifying the filtered hydrogen-oxygen mixed gas, wherein the humidification device further comprises at least an output tube having a plurality of holes, and the filtered hydrogen-oxygen mixed gas is received by the humidification device and outputted through the plurality of holes of the output tube to generate the humidified hydrogen-oxygen mixed gas;
a pump device configured for generating a negative pressure in the water tank in order to pump the supplementary water from the humidification device through the condensate filter to the water tank, such that the filtered electrolyte in the condensate filter is flushed back to the electrolysis device;
wherein the condensate filter is capable to receive the supplementary water from the humidification device to flush the filtered electrolyte out of the condensate filter.

9. The gas generator of claim 8, further comprising a supplemental filter coupled to the humidification device to filter the filtered hydrogen-oxygen mixed gas, wherein the supplemental filter comprises a housing and a filtering module, the housing comprises a input and an output, the input is configured to receive the filtered hydrogen-oxygen mixed gas into the housing, the filtering module is disposed in the housing to filter the filtered hydrogen-oxygen mixed gas, and the output outputs the filtered hydrogen-oxygen mixed gas from the housing after the filtering module filtering the filtered hydrogen-oxygen mixed gas.

10. The gas generator of claim 8, further comprising a water tank accommodating the electrolyzed water and the electrolysis device, and a cooling device coupled to the water tank for cooling. the electrolyzed water.

11. The gas generator of claim 10, further comprising an atomized gas mixing tank coupled to the humidification device, the atomized gas mixing tank generating an atomized gas and mixing the atomized gas with the filtered hydrogen-oxygen mixed gas to form a healthy gas.

12. The gas generator of claim 10, wherein the atomized gas mixing tank is vertically spaced apart from the water tank.

13. A gas generator comprising:
a water tank accommodating electrolyzed water;
an electrolysis device having a case disposed within the water tank, the electrolysis device configured to electrolyze the electrolyzed water to generate a hydrogen-oxygen mixed gas;
a condensate filter filtering electrolyte in the hydrogen oxygen mixed gas to generate a filtered hydrogen-oxygen mixed gas, wherein the condensate filter is capable to receive a supplementary water;
a humidification device accommodating the supplementary water and coupled to the condensate filter for humidifying the filtered hydrogen-oxygen mixed gas to generate a humidified hydrogen-oxygen mixed gas; and
a pump device configured to drive the supplementary water from the humidification device through the condensate filter to the water tank;
wherein the humidification device further comprises at least an output tube having a plurality of holes, and the filtered hydrogen-oxygen mixed vas is received by the humidification device and outputted through the plurality of holes of the output tube to generate the humidified hydrogen-oxygen mixed gas.

* * * * *